(12) United States Patent
Nilsen et al.

(10) Patent No.: US 9,815,785 B2
(45) Date of Patent: Nov. 14, 2017

(54) ENANTIOMERIC SEPARATION AND PURIFICATION OF 2,3,4,9-TETRAHYDRO-1H-CARBAZOLE-4-CARBOXYLIC ACID AMIDE DERIVATIVES

(71) Applicant: GE HEALTHCARE LIMITED, Little Chalfont, Buckinghamshire (GB)

(72) Inventors: Sondre Nilsen, Oslo (NO); Dimitrios Mantzilas, Oslo (NO)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 14/905,649

(22) PCT Filed: Jul. 17, 2014

(86) PCT No.: PCT/EP2014/065360
§ 371 (c)(1),
(2) Date: Jan. 15, 2016

(87) PCT Pub. No.: WO2015/007834
PCT Pub. Date: Jan. 22, 2015

(65) Prior Publication Data
US 2016/0168091 A1 Jun. 16, 2016

(30) Foreign Application Priority Data
Jul. 17, 2013 (GB) .................... 1312768.3

(51) Int. Cl.
| C07D 209/84 | (2006.01) |
| C07D 209/88 | (2006.01) |
| C07D 491/048 | (2006.01) |
| C07D 491/052 | (2006.01) |
| C07D 491/044 | (2006.01) |
| C07D 495/04 | (2006.01) |
| A61K 51/04 | (2006.01) |
| G01N 33/60 | (2006.01) |

(52) U.S. Cl.
CPC ........ *C07D 209/84* (2013.01); *A61K 51/0446* (2013.01); *C07D 209/88* (2013.01); *G01N 33/60* (2013.01)

(58) Field of Classification Search
CPC ............... C07D 209/84; C07D 209/88; C07D 491/048; C07D 491/052; C07D 491/044; C07D 495/04; A61K 51/0446
USPC .................. 548/448, 441, 432, 430
See application file for complete search history.

(56) References Cited

U.S. PATENT DOCUMENTS

| 4,808,599 | A | 2/1989 | Dubroeucq et al. |
| 6,451,795 | B1 | 9/2002 | Marguet et al. |
| 2011/0070161 | A1 | 3/2011 | Achanath et al. |

FOREIGN PATENT DOCUMENTS

| CN | 1069726 A | 3/1993 | |
| CN | 1095712 A | 11/1994 | |
| CN | 102448933 A | 5/2012 | |
| CN | 102834379 A | 12/2012 | |
| EP | 3022178 A1 | 5/2016 | |
| IN | WO 2011117421 A1 * | 9/2011 | ......... A61K 51/0446 |
| WO | 9414772 A1 | 7/1994 | |
| WO | 2007057705 A1 | 5/2007 | |
| WO | 2010/109007 A2 | 9/2010 | |
| WO | 2011117421 A1 | 9/2011 | |
| WO | 2012038532 A1 | 3/2012 | |
| WO | 2012041953 A1 | 4/2012 | |
| WO | 2012080349 A1 | 6/2012 | |
| WO | 2015/007834 A1 | 1/2015 | |

OTHER PUBLICATIONS

"Separation and Purification". Encyclopdia Britannica Online. Encyclopædia Britannica Inc., Nov. 4, 2011. Web. Feb. 15, 2017 <https://www.britannica.com/science/separation-and-purification>.*
Okubu et al., "A Design Synthesis and Structure-Activity Relationships of Novel Tetracyclic Compounds as Peripheral Benzodiazepine Receptor ligands", Bioorganic & Medicinal Chemistry, vol. No. 12, Issue No. 13, pp. 3569-3580, Mar. 25, 2004.
Nashat et al., "Expression of the Translocator Protein of 18 kDA by Microglia, Macrophages and Astrocytes Based on Immunohistochemical Localization in Abnormal human Brain", Neuropathology and Applied Neurobiology, vol. No. 35, Issue No. 3, pp. 306-328, 2009.
Wadsworth et al., "[18F]GE-180: A Novel Fluorine-18 Labelled PET Tracer for Imaging Translocator Protein 18 kDa (TSPO)", Bioorganic & Medicinal Chemistry Letters, vol. No. 22, Issue No. 3, pp. 1308-1313, Feb. 2, 2012.
Great Breton Search Report issued in connection with corresponding GB Application No. GB1312768.3 dated Jan. 10, 2014.
PCT Search Report and Written Opinion issued in connection with corresponding Application No. PCT/EP2014/065360 dated Aug. 27, 2014.
International Preliminary Report on Patentability received for PCT Patent Application No. PCT/EP2014/065360, dated Jan. 19, 2016, 6 pages.
Office Action received for European Patent Application No. 14742481.6, dated Jan. 27, 2017, 5 pages.
Office Action received for Chinese Patent Application No. 201480040621.0, dated Apr. 12, 2017, 25 pages (15 pages of English Translation + 10 pages of Official Copy).

* cited by examiner

*Primary Examiner* — Matthew Coughlin
*Assistant Examiner* — Sagar Patel
(74) *Attorney, Agent, or Firm* — Wood IP LLC

(57) ABSTRACT

A method for the purification of cyclic indole compounds that provides advantages over previously-known methods. Using the method of the present invention allows for the facile preparation of a good quality solid form of these compounds.

13 Claims, No Drawings

ENANTIOMERIC SEPARATION AND PURIFICATION OF 2,3,4,9-TETRAHYDRO-1H-CARBAZOLE-4-CARBOXYLIC ACID AMIDE DERIVATIVES

CROSS-REFERENCE TO RELATED APPLICATIONS

This application is a national stage application under 35 U.S.C. §371(c) of prior filed, co-pending PCT application serial number PCT/EP2014/065360, filed on Jul. 17, 2014, which claims priority to GB Patent Application No. 1312768.3, titled "WORK-UP PROCEDURE" filed Jul. 17, 2013. The above-listed applications are herein incorporated by reference.

FIELD OF THE INVENTION

Embodiments of the invention relate to a novel work-up procedure used in the synthesis of a particular class of chemical compounds. The compounds are fused cyclic indole compounds that find use in particular as direct labelling precursor compounds in the radiosynthesis of certain $^{18}$F-labelled positron-emission tomography (PET) tracers.

BACKGROUND OF THE INVENTION

Translocator protein (TSPO) is an 18 kD protein that is known to be mainly localised in peripheral tissues and glial cells but its physiological function remains to be clearly elucidated. Subcellularly, TSPO is known to localise on the outer mitochondrial membrane, indicating a potential role in the modulation of mitochondrial function and in the immune system. It has furthermore been postulated that TSPO is involved in cell proliferation, steroidogenesis, calcium flow and cellular respiration.

In studies examining the expression of TSPO in normal and diseased tissue, Cosenza-Nashat et al (2009 Neuropathol Appl Neurobiol; 35(3): 306-328) confirmed that TSPO expression in normal brain is minimal. This same paper demonstrated that in disease states elevated TSPO was present in parenchymal microglia, macrophages and some hypertrophic astrocytes, but the distribution of TSPO varied depending on the disease, disease stage and proximity to the lesion or relation to infection. Microglia and macrophages are the predominant cell type expressing TSPO in diseased brains, and astrocytes can also express TSPO in humans.

Ligands having affinity for TSPO are known in the art. A class of indole compounds having affinity for TSPO ($IC_{50}$ values for most active compounds of between 0.2 nM and 5.0 nM) is disclosed in U.S. Pat. No. 6,451,795 as useful for the prevention or treatment of peripheral neuropathies and for the treatment of central neurodegenerative diseases. Okubu et al (Bioorg Med Chem 2004; 12: 3569-80) describe the design, synthesis and structure of a group of tetracyclic indole compounds having affinity for TSPO ($IC_{50}$ values as low as about 0.4 nM).

A class of labelled tetracyclic indole derivatives was reported by Arstad et al (WO 2007/057705) as having nanomolar affinity for TSPO and therefore suitable for in vivo imaging of TSPO, e.g. in conditions such as Parkinson's disease, Alzheimer's disease, multiple sclerosis, neuropathic pain, arthritis, asthma, atherosclerosis and cancer. Radiolabelled tricyclic indole derivatives were disclosed by Wadsworth et al (WO 2010/109007) and reported to have nanomolar affinity in an in vitro assay as well as good metabolic stability and uptake in the brain in vivo sufficiently high and specific to indicate suitability of these compounds for application in in vivo imaging of TSPO expression in the central nervous system (CNS). Wadsworth et al (Bioorg Med Chem Letts 2012; 22: 1308-1313) and Achanath et al (WO 2011/117421) went on to report that these properties for in vivo imaging of TSPO in the brain were even more favourable in the S-enantiomer as compared to the racemate.

Purification of separated enantiomers of the above-described cyclic indole derivatives has presented challenges for the present inventors, in particular when trying to reproducibly obtain the purified enantiomer in a solid form when gram-sized batches are being processed. The present inventors have encountered difficulties when trying to obtain separated enantiomer in good quality solid form using the known rotary evaporation method, even when different solvents and/or different rotary evaporation equipment and/or rotary evaporation conditions are tried. There is therefore a need for an improved method for the purification of these compounds.

SUMMARY OF THE INVENTION

Embodiments of the invention provide a method for the purification of cyclic indole compounds that provides advantages over currently used methods. Using the method of the present invention allows for the facile preparation of a good quality powder form of these compounds that is very easy to dispense. The method of the invention is faster and more reproducible compared to current methods.

DETAILED DESCRIPTION

In a first aspect an embodiment of the invention provides a method comprising (i) separating an S-enantiomer from an R-enantiomer wherein the S-enantiomer and the R-enantiomer are provided in a racemic mixture and wherein each of the S-enantiomer and the R-enantiomer is a compound of Formula I:

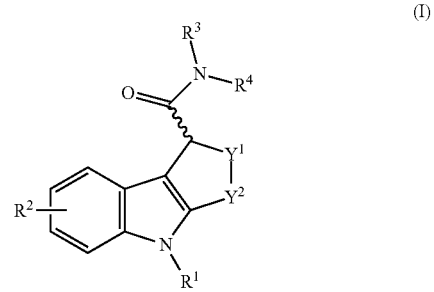

wherein:
$R^1$ is $C_{1-4}$ alkylene-LG wherein LG is a leaving group;
$R^2$ is hydrogen, hydroxyl, halo, cyano, $C_{1-3}$ alkyl, $C_{1-3}$ alkoxy, $C_{1-3}$ fluoroalkyl, or $C_{1-3}$ fluoroalkoxy;
$R^3$ and $R^4$ are independently $C_{1-3}$ alkyl, $C_{7-10}$ aralkyl, or $R^3$ and $R^4$, together with the nitrogen to which they are attached, form a nitrogen-containing $C_{4-6}$ aliphatic ring optionally comprising 1 further heteroatom selected from nitrogen, oxygen and sulfur;
$Y^1$ is O, S, SO, $SO_2$ or $CH_2$;
$Y^2$ is $CH_2$, $CH_2$—$CH_2$, $CH(CH_3)$—$CH_2$, $CH_2$—$CH_2$—$CH_2$ or CH—(CH—$CH_2$—CH—$CH_2$)—CH;

the variable bond is above the plane for the S-enantiomer and below the plane for the R-enantiomer as illustrated respectively in Formulas I-S and I-R:

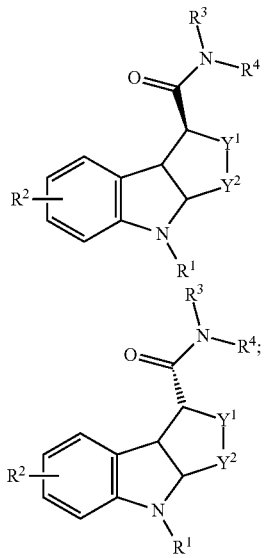

(ii) dissolving one of the separated enantiomers in a suitable organic solvent; (iii) precipitating the dissolved enantiomer out of the solution obtained in step (ii) wherein the precipitating step comprises addition of water; (iv) isolating the precipitate obtained in step (iii).

The term "separating" in the context of the method of the present invention refers to any method suitable for the separation from a racemic mixture of an S-enantiomer from and R-enantiomer, also commonly referred to in the art as "chiral resolution", "chiral separation" or "optical resolution". Various means are known for separating enantiomers from a racemate, for example crystallisation and chromatography. For the method of the present invention chromatography is selected and in particular supercritical fluid chromatography (SFC). The term "supercritical fluid chromatography" refers to a form of normal phase chromatography wherein the mobile phase is comprised of high pressure liquid or supercritical carbon dioxide and a modifier such as methanol, ethanol, isopropyl alcohol, acetonitrile or chloroform.

Formula I in the case of the "S-enantiomer" is Formula I-S:

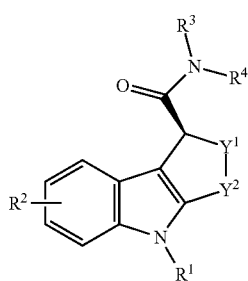

wherein each of $R^{1-4}$ and $Y^{1-2}$ is as defined for Formula I.

Formula I in the case of the "R-enantiomer" is Formula I-R:

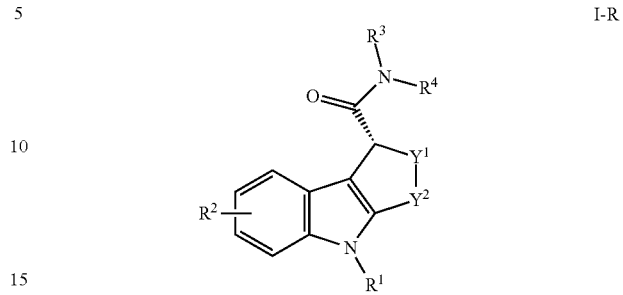

wherein each of $R^{1-4}$ and $Y^{1-2}$ is as defined for Formula I and is the same as for Formula I-S when both are present in the same racemate.

The term "racemic mixture" or "racemate" is a mixture that has equal amounts of S- and R-enantiomers of a chiral molecule. The racemic mixture in the method of the present invention comprises equal amounts of the S-enantiomer and the R-enantiomer.

The term "alkylene" refers to the bivalent group —$(CH_2)_n$— wherein n may be an integer from 1-4.

The term "leaving group" refers to an atom or group of atoms that is displaced as a stable species during a substitution or displacement radiofluorination reaction. Examples of suitable leaving groups are the halogens chloro, bromo and iodo, and the sulfonate esters mesylate, tosylate nosylate and triflate. In an embodiment, the leaving group is selected from mesylate, tosylate and triflate, and is more particularly mesylate.

The term "hydroxyl" refers to the group —OH.

The term "halogen" or "halo-" means a substituent selected from fluorine, chlorine, bromine or iodine.

The term "cyano" refers to the group —CN.

Unless otherwise specified, the term "alkyl" alone or in combination, means a straight-chain or branched-chain alkyl radical containing from 1 to 3 carbon atoms. Examples of such radicals include, methyl, ethyl, and propyl.

Unless otherwise specified, the term "alkoxy" means an alkyl radical as defined above comprising an ether linkage, and the term "ether linkage" refers to the group —C—O—C—. Examples of suitable alkyl ether radicals include, methoxy, ethoxy, and propoxy.

"Fluoroalkyl" and "fluoroalkoxy" are alkyl and alkoxy groups, respectively, as defined above substituted with one or more fluorine atoms. Suitably the fluorine replaces a hydrogen at the terminal end of the radical, i.e. -alkylene-fluoro or -alkoxylene-fluoro.

The term "aralkyl" refers to the group -alkylene-phenyl wherein alkylene is as defined above.

A "nitrogen-containing $C_{4-6}$ aliphatic ring" is a saturated $C_{4-6}$ alkyl ring comprising a nitrogen heteroatom. Examples include pyrolidinyl, piperidinyl and morpholinyl rings.

The term "heteroatom" refers to a non-carbon atom that replaces a carbon in the backbone of the molecular structure.

The following table illustrates the structure of Formula I for each $Y^2$:

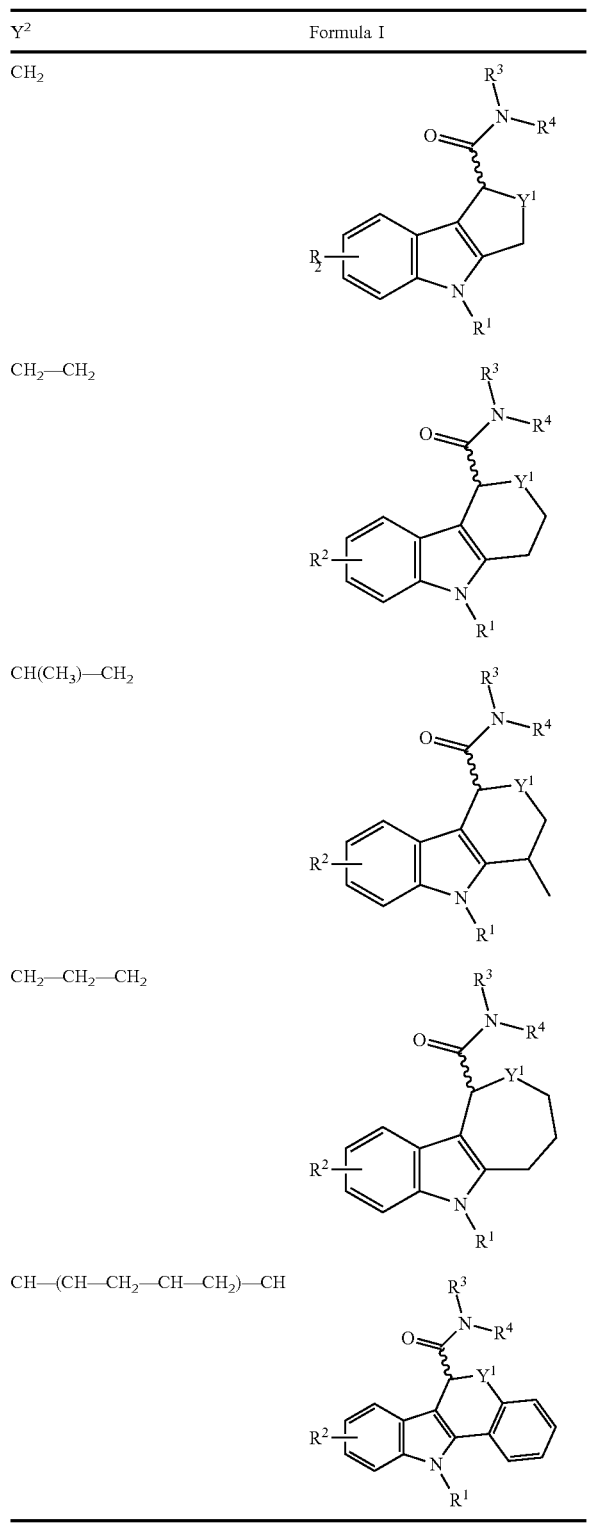

The term "suitable organic solvent" refers to any organic solvent in which the enantiomer of Formula I can be dissolved. Suitable such organic solvents include alcohols, 1,4-dioxane, tetrahydrofuran or acetonitrile. The term "alcohols" includes well-known alcohol solvents such as ethanol, methanol, isopropanol, butanol and propanol.

The term "dissolving" refers to the process whereby a substance becomes incorporated into a liquid so as to form a solution. In order for the dissolving step of the method of the invention to result in a solution of the separated enantiomer of Formula I in the suitable organic solvent it may be required to apply heat. Suitably heat up to about 60° C. may be applied but in the range 30-40° C. is typically sufficient to assist dissolution.

The term "precipitating" refers to the formation of a solid form of one or more solutes in a solution. The solid formed is referred to in the art as the "precipitate" and the reagent used to form the solid is referred to in the art as the "precipitant". In the method of the present invention water is the precipitant. In order for the precipitating step to go to completion it may also be necessary to stir the solution and/or to apply heating and/or to apply cooling. In a similar way to the dissolving step temperatures up to about 60° C. may be applied for heating. When cooling is applied the range 0-10° C. is typically suitable.

The term "isolating" refers to the process wherein the precipitate is separated from the remaining precipitate-free solution (often referred to in the art as the "supernate"). This can be done using any well-known method for the separation of a solid from a liquid but is most suitably carried out by filtration.

An additional benefit with the method of the first aspect of the embodiment of the present invention is that it is not required to carry out any additional purification steps following isolation of the precipitate in step (iv). With the known rotary evaporation method the present inventors observed an up-concentration of any impurities present in the reagents used. Additional purification steps were therefore required in order to result in precursor of Formula I-S or I-R with an acceptable impurity profile. Even with such further purification following known evaporation techniques, residual impurities remain, necessitating reporting and qualification according to the ICH guidelines (which can be found at http://www.ich.org/products/guidelines/quality/article/quality-guidelines.html). This need for reporting and qualification is not required with the methods of the present invention. Therefore, a facile means to obtain a good quality and solid form of compound of Formula I-S or I-R with an improved impurity profile is provided.

$R^1$ of Formula I may be bromo, chloro, iodo, tosylate, mesylate or triflate, more particularly bromo, tosylate, mesylate or triflate and may be mesylate.

$R^2$ of Formula I in an embodiment is hydrogen, halo, $C_{1-3}$ alkoxy or $C_{1-3}$ fluoroalkoxy, more particularly hydrogen, halo or $C_{1-3}$ alkoxy and may be hydrogen, fluoro or methoxy. Where $R^2$ is a substituent (i.e. not hydrogen) it is at the 5- or 6-position in an embodiment, and is more particularly selected from 5-methoxy, 6-methoxy, 5-fluoro and 6-fluoro.

$R^3$ and $R^4$ of Formula I are independently methyl, ethyl or benzyl in an embodiment. In one embodiment $R^3$ is methyl and $R^4$ is benzyl. In another embodiment $R^3$ and $R^4$ are both ethyl.

In one embodiment $Y^1$ of Formula I is S. When $Y^1$ is S, $Y^2$ of Formula I is more particularly —CH—(CH—CH$_2$—CH—CH$_2$)—CH—.

In another embodiment $Y^1$ of Formula I is CH$_2$. When $Y^1$ of Formula I is CH$_2$ $Y^2$ of Formula I is more particularly —CH$_2$—CH$_2$—.

In one embodiment of Formula I: $R^1$ is bromo, chloro, iodo, tosylate, mesylate or triflate, more particularly bromo, tosylate, mesylate or triflate and in another embodiment mesylate; $R^2$ is hydrogen, halo, $C_{1-3}$ alkoxy or $C_{1-3}$ fluoroalkoxy, may be hydrogen, halo or $C_{1-3}$ alkoxy and more particularly hydrogen, fluoro or methoxy; $R^3$ and $R^4$ are independently methyl, ethyl or benzyl, particularly $R^3$ is methyl and $R^4$ is benzyl, alternatively $R^3$ and $R^4$ are ethyl; $Y^1$ of Formula I is S; and, $Y^2$ of Formula I is —CH—(CH—CH$_2$—CH—CH$_2$)—CH—.

In another embodiment of Formula I: $R^1$ of is bromo, chloro, iodo, tosylate, mesylate or triflate, particularly bromo, tosylate, mesylate or triflate and more particularly mesylate; $R^2$ is hydrogen, halo, $C_{1-3}$ alkoxy or $C_{1-3}$ fluoroalkoxy, particularly hydrogen, halo or $C_{1-3}$ alkoxy and more particularly hydrogen, fluoro or methoxy; $R^3$ and $R^4$ are independently methyl, ethyl or benzyl, more particularly $R^3$ is methyl and $R^4$ is benzyl, alternatively $R^3$ and $R^4$ are ethyl; $Y^1$ is CH$_2$; and, $Y^2$ is —CH$_2$—CH$_2$—.

Each of the above-defined embodiments of Formula I is equally applicable to the compounds of Formula I-S and Formula I-R.

Examples of compounds of Formula I include the following:

1

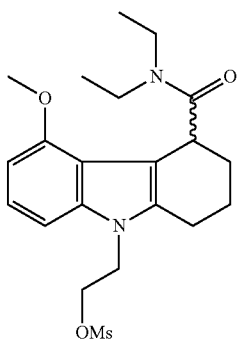

2

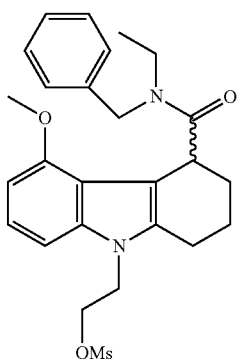

3

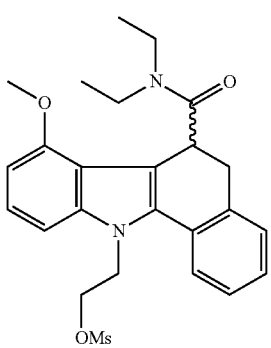

4

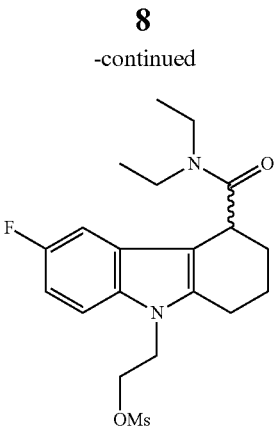

5

6

Wherein OMs represents mesylate.

In each case, the S-enantiomer is more particular. The experimental examples below relate to compound 1 of Formula I.

Compounds of Formula I can be obtained by methods known in the art.

Arstad et al (WO 2007/057705) report that fused tetracyclic indole compounds of Formula I may be obtained by adapting the methods described by Okubo et al (Bioorg Med Chem 2004; 12: 3569-80).

Wadsworth et al (WO 2010/109007) report how to obtain fused tricyclic indole compounds of Formula I using one of Scheme 1 or Scheme 2 below:

Scheme 1
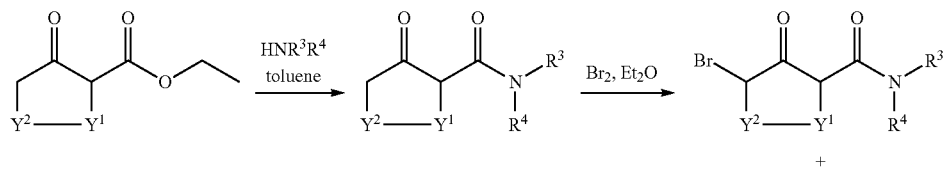
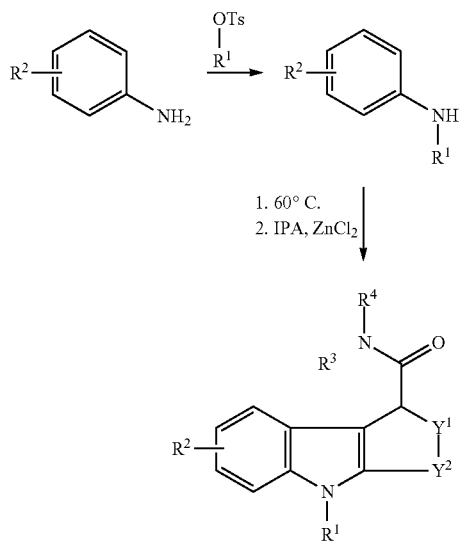
Wherein Et$_2$O=diethyl ether; IPA=isopropyl alcohol; OTs=tosylate.
Alternatively, where R$^2$ of Formula I is at the top position on the ring, the general synthetic route illustrated in Scheme 2 below can be used:
Scheme 2
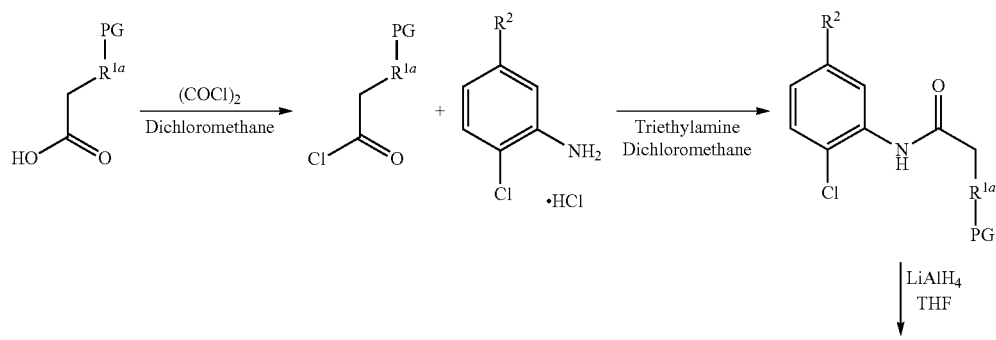

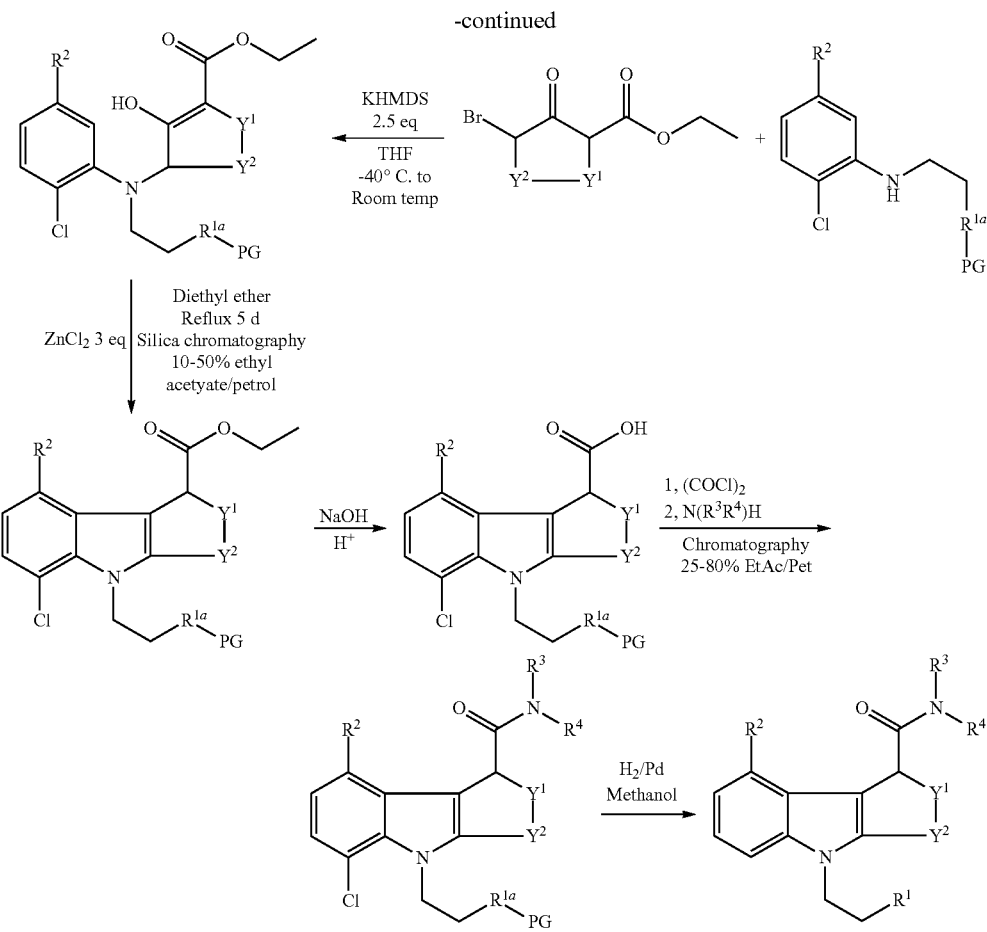

Wherein PG=protecting group; THF=tetrahydrofuran; KHMDS=Potassium bis(trimethylsilyl)amide; EtAc=ethyl acetate; Pet=petroleum ether.

In the above Scheme 1 and Scheme 2, each of $R^{1-4}$, $Y^1$ and $Y^2$ are as defined herein for Formula I. In Scheme 2 the group "—$R^{11a}$—PG", represents a protected $R^1$ group wherein $R^1$ is as defined herein for Formula I and PG is a protecting group. Suitable protecting groups are well-known in the art and are discussed in more detail by Theodora W. Greene and Peter G. M. Wuts in "Protective Groups in Organic Synthesis" (Fourth Edition, John Wiley & Sons, 2007).

Achanath et al (WO 2011/117421) describe methods suitable for carrying out the separating step of embodiments of the present invention including high performance liquid chromatography (HPLC), supercritical fluid chromatography (SFC), simulated bed chromatography (SBC). A detailed assessment of the various techniques that may be applied for enantiomeric separation can be found in "Chiral Separation Techniques: a Practical Approach" (2007 Wiley; Subramanian, Ed.). In an embodiment, the separating step of the present invention is carried out using SFC.

In an embodiment the organic solvent used in the method of the present invention is ethanol, methanol, isopropanol, butanol, propanol, 1,4-dioxane, tetrahydrofuran or acetonitrile, more particularly propanol, ethanol, methanol or acetonitrile.

In a second aspect, embodiments of the present invention provides a method to obtain an $^{18}$-labelled positron emission tomography (PET) tracer of Formula II:

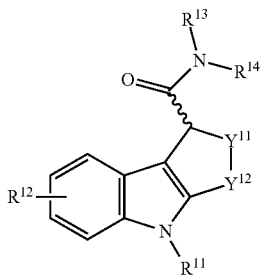

(II)

wherein $R^{11}$ is $C_{1-3}$ alkylene$^{18}$F; and wherein each of $R^{12}$-$R^{14}$ and $Y^{11}$-$Y^{12}$ and the variable bond is as defined herein for $R^2$-$R^4$ and $Y^1$-$Y^2$ of Formula I; wherein the method comprises the method as defined hereinabove, followed by reaction of a solution of the precipitate obtained in step (iv) with a suitable source of $^{18}$F-fluoride.

A "PET tracer" is a chemical compound that comprises a positron-emitting isotope, wherein the chemical compound is designed to target a particular physiology or pathophysiology in a biological system. The presence of the positron-emitting isotope allows the PET tracer to be detected following administration to the biological system and thereby facilitate detection of the particular physiology or pathophysiology. The PET tracer of Formula II is either the S- or the R-enantiomer.

The term "suitable source of $^{18}$F-fluoride" means $^{18}$F-fluoride in a chemical form suitable for displacing LG of Formula I in a nucleophilic substitution reaction to result in a compound of Formula II. $^{18}$F-fluoride is normally obtained as an aqueous solution from the nuclear reaction $^{18}$O(p,n)$^{18}$F and is made reactive by the addition of a cationic counterion and the subsequent removal of water. Suitable cationic counterions should possess sufficient solubility within the anhydrous reaction solvent to maintain the solubility of $^{18}$F$^-$. Suitable counterions include large but soft metal ions such as rubidium or caesium, potassium complexed with a cryptand such as Kryptofix™ 222 (K222), or tetraalkylammonium salts. A counterion is potassium complexed with a cryptand such as K222 because of its good solubility in anhydrous solvents and enhanced $^{18}$F$^-$ reactivity.

A detailed discussion of well-known $^{18}$F labelling techniques can be found in Chapter 6 of the "Handbook of Radiopharmaceuticals" (2003; John Wiley and Sons: M. J. Welch and C. S. Redvany, Eds.).

In an embodiment, the method to prepare the compound of Formula II is automated. [$^{18}$F]-radiotracers may be conveniently prepared in an automated fashion by means of an automated radiosynthesis apparatus. There are several commercially-available examples of such apparatus, including Tracerlab™ and Fastlab™ (both from GE Healthcare Ltd.). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps.

Examples of compounds of Formula II include either the S- or the R-enantiomer of the following compounds:

7

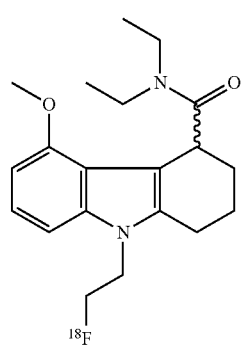

8

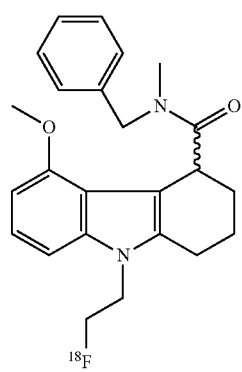

-continued

9

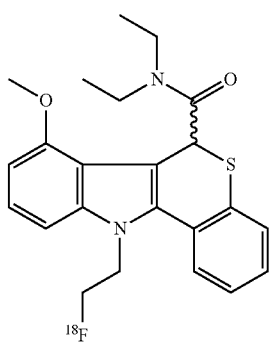

10

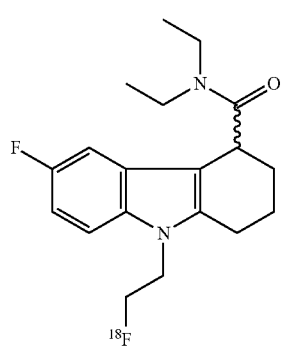

11

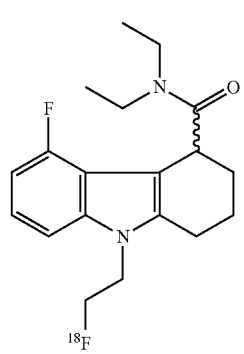

12

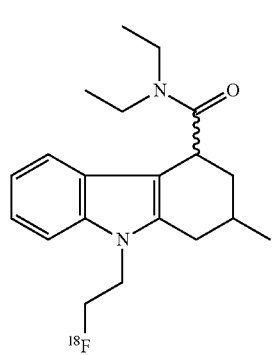

The S-enantiomer of each of the above-illustrated compounds is selected in an embodiment.

A third aspect of an embodiment the present invention is a compound of Formula I-S or of Formula I-R obtainable according to the first aspect of an embodiment of the invention. The method of the first aspect of the present invention allows for the straightforward preparation of an enantiomer of either Formula I-S or I-R in a good quality powder form that is very easy to dispense.

A fourth aspect of embodiment of the present invention is a compound of Formula II obtainable according to the second aspect of an embodiment of the invention.

Embodiments of the invention is now illustrated by a series of non-limiting examples.

EXAMPLES

Example 1 describes the synthesis of a racemic mixture of the S-enantiomer and the R-enantiomer of compound 1 of Formula I.

Example 2 describes the separation of the S-enantiomer and the R-enantiomer of compound 1 of Formula I.

Comparative Example 3 describes the purification of the S-enantiomer of compound 1 of Formula I by rotary evaporation. The resultant purified S-enantiomer was very difficult to obtain in solid form by rotary evaporation, even when the method was adapted by trying different solvents and rotary evaporation parameters.

Example 4 describes the purification of the S-enantiomer of compound 1 of Formula I by precipitation according to the method of the invention.

List of Abbreviations Used in the Examples

DMF dimethyl formamide
H hour(s)
HPLC high-performance liquid chromatography
IPA isopropyl alcohol
MeCN acetonitrile
MeOH methanol
min minute(s)
NMR nuclear magnetic resonance
RT room temperature
SFC supercritical fluid chromatography
THF tetrahydrofuran

EXAMPLES

Example 1: Synthesis of a racemic mixture of the S-enantiomer and the R-enantiomer of compound 1 of Formula I

Example 1(a): Benzyloxy Acetyl Chloride

To benzyloxyacetic acid (10.0 g, 60.0 mmol, 8.6 mL) in dichloromethane (50 mL) was added oxalyl chloride (9.1 g, 72.0 mmol, 6.0 mL) and DMF (30.0 mg, 0.4 mmol, 32.0 µL) and stirred at RT for 3 h. There was initially a rapid evolution of gas as the reaction proceeded but evolution ceased as the reaction was complete. The dichloromethane solution was concentrated in vacuo to give a gum. This gum was treated with more oxalyl chloride (4.5 g, 35.7 mmol, 3.0 mL), dichloromethane (50 mL), and one drop of DMF. There was a rapid evolution of gas and the reaction was stirred for a further 2 h. The reaction was then concentrated in vacuo to afford 11.0 g (quantitative) of Benzyloxy acetyl chloride as a gum. The structure was confirmed by $^{13}$C NMR (75 MHz, CDCl$_3$) $\delta_C$ 73.6, 74.8, 128.1, 128.4, 128.6, 130.0, and 171.9.

Example 1(b): 2-Benzyloxy-N-(2-chloro-5-metnhoxy-phenyl)acetamide

Benzyloxy acetyl chloride (11.0 g, 60.0 mmol) and 2-chloro-5-methoxyaniline hydrochloride (11.7 g, 60.2 mmol) in dichloromethane (100 mL) at 0° C., was stirred and triethylamine (13.0 g 126.0 mmol, 18.0 mL) added slowly over 15 min. The stirred reaction was allowed to warm to RT over 18 h. There was a heavy precipitation of triethylamine hydrochloride. The dichloromethane solution was washed with 10% aqueous potassium carbonate (50 mL), dried over magnesium sulfate and concentrated in vacuo to afford 18.9 g (quantitative) of 2-Benzyloxy-N-(2-chloro-5-methoxy-phenyl) acetamide as a gum. The structure was confirmed by $^{13}$C NMR (75 MHz, CDCl$_3$): $\delta_C$ 55.6, 69.6, 73.6, 106.2, 111.1, 114.1, 127.7, 128.3, 128.6, 129.2, 134.6, 136.5, 158.9, and 167.7.

Example 1(c): (2-Benzyloxy-ethyl)-(2-chloro-5-methoxyphenyl)amine

2-Benzyloxy-N-(2-chloro-5-methoxy-phenyl) acetamide (18.9 g, 62.0 mmol) in THF (100 mL) was stirred and lithium aluminium hydride (4.9 g, 130.0 mmol) was added slowly over 15 min. There was a rapid evolution of hydrogen gas as the first of the lithium aluminium hydride was added. The reaction was then heated to reflux for 4 h and allowed to stand at RT over the weekend. The reaction was then quenched by the dropwise addition of water (50 mL) to the stirred solution. There was a violent evolution of hydrogen causing the reaction mixture to reflux. The reaction was then concentrated in vacuum to a slurry. Water (200 mL) and ethyl acetate (200 mL) were added and the mixture vigorously shaken. The reaction was then filtered through celite to remove the precipitated aluminium hydroxide and the ethyl acetate solution was separated, dried over magnesium sulfate and concentrated in vacuo to afford 18.4 g (quantitative) of (2-Benzyloxy-ethyl)-(2-chloro-5-methoxyphenyl)amine as a gum. The structure was confirmed by $^{13}$C NMR (75 MHz, CDCl$_3$) $\delta_C$ 43.3, 55.3, 68.2, 73.0, 98.1, 101.8, 111.6, 127.6, 127.7, 128.4, 129.3, 137.9, 144.8, and 159.5.

Example 1(d): 3-Bromo-2-hydroxy-cyclohex-1-enecarboxylic Acid Ethyl Ester

Ethyl 2-oxocyclohexanecarboxylate (30 g, 176 mmol, 28 mL) was dissolved in diethyl ether (30 mL) and cooled to 0° C. under nitrogen. Bromine (28 g, 176 mmol, 9.0 mL) was added dropwise over 15 min and the reaction mixture was allowed to warm to RT over 90 min. The mixture was slowly poured into ice-cold saturated aqueous potassium carbonate (250 mL) and extracted with ethyl acetate (3×200 mL). The combined organic layers were dried over magnesium sulfate, filtered, concentrated in vacuo and dried on the vacuum line for 18 h to afford 41.4 g (94%) of 3-Bromo-2-hydroxy-1-enecarboxylic acid ethyl ester as a yellow oil. The structure was confirmed by $^{13}$C NMR (75 MHz, CDCl$_3$): $\delta_C$ 14.1, 17.7, 21.8, 32.0, 60.0, 60.8, 99.7, 166.3, and 172.8.

Example 1(e): 3[(2-Benzyloxy-ethyl)-(2-chloro-5-methoxy-phenyl)-amino]-2-hydroxy-cyclohex-1-ene Carboxylic Acid Ethyl Ester (2-Benzyloxy-ethyl)-(2-chloro-5-methoxyphenyl)amine (10.0 g, 34.2 mmol) was stirred in dry THF (100 mL) at −40° C. under nitrogen and potassium bis(trimethylsilyl) amide (143.0 mL of a 0.5 M solution in toluene, 72.0 mmol) was added over 30 min. 3-bromo-2-hydroxycyclohex-1-enecarboxylic acid ethyl ester (8.5 g, 34.2 mmol) in dry THF (10 mL) was then added and allowed to warm to RT over a period of 1.5 h. Acetic acid (10.0 g, 166 mmol, 10.0 mL) was added and concentrated in vacuo to remove the THF. Ethyl acetate (200 mL) and 10% aqueous potassium carbonate (100 mL) was added and the mixture vigorously shaken. The ethyl acetate solution was separated, dried over magnesium sulfate and concentrated in vacuo to afford 16.5 g (quantitative) of 3[(2-Benzyloxy-ethyl)-(2-chloro-5-methoxy-phenyl)-amino]-2-hydroxy-cyclohex-1-ene carboxylic acid ethyl ester as a gum which was used crude in the next step. HPLC (Gemini 150×4.6 mm, 50-95% methanol/water over 20 min) of crude reaction mixture, 18.9 min (38%), 19.2 min (25%), 23.1 min (28%).

One component of the reaction was isolated $^{13}$C NMR (75 MHz, CDCl$_3$) $\delta_C$ 14.3, 20.6, 21.8, 26.4, 38.6, 43.0, 55.8, 60.5, 68.7, 73.3, 93.4, 106.3, 108.2, 119.3, 121.5, 127.5, 127.6, 128.3, 135.7, 137.0, 137.9, 155.7, and 175.0.

Example 1(f): 9-(2-Benzyloxy-ethyl)-8-chloro-5-methoxy-2,3,4,9,-tetrahydro-1H-carbazole-4-carboxylic Acid Ethyl Ester Zinc chloride (7.1 g, 52.0 mmol) was added to 3[(2-Benzyloxy-ethyl)-(2-chloro-5-methoxy-phenyl)-amino]-2-hydroxy-cyclohex-1-ene carboxylic acid ethyl ester (8.0 g, 17.0 mmol) in dry diethyl ether (150 mL) under nitrogen and heated at reflux for 5.5 h. As the reaction was refluxed a thick brown dense oil formed in the reaction. The reaction was then cooled and the supernatant diethyl ether decanted off, ethyl acetate (100 mL) was added, washed with 2 N HCl (50 mL) and with 10% aqueous potassium carbonate (50 mL). The diethyl ether layer was separated, dried over magnesium sulfate and concentrated in vacuo to afford an oil (2.0 g). The crude material was purified by silica gel chromatography eluting with petrol (A): ethyl acetate (B) (10-40% (B), 340 g, 22 CV, 150 mL/min) to afford 1.8 g of 9-(2-Benzyloxy-ethyl)-8-chloro-5-methoxy-2,3,4,9,-tetrahydro-1H-carbazole-4-carboxylic acid ethyl ester. The thick dense brown layer was treated with ethyl acetate (100 mL) and 2 N HCl (50 mL). The ethyl acetate solution was separated, washed with 10% aqueous potassium carbonate (50 mL), dried over magnesium sulfate and concentrated in vacuo to give an oil (5.2 g). Diethyl ether (100 mL) and anhydrous zinc chloride (7.0 g) were added. The mixture was heated at reflux for a further 5 days. The ether layer was decanted off from the dark gum, was washed with 2 N HCl (50 mL), dried over magnesium sulfate and concentrated in vacuo to give a gum (2.8 g). This gum was purified by silica gel chromatography eluting with petrol (A): ethyl acetate (B) (5-35% (B), 340 g, 150 mL/min) to afford 2.1 g of 9-(2-Benzyloxy-ethyl)-8-chloro-5-methoxy-2,3,4,9,-tetrahydro-1H-carbazole-4-carboxylic acid ethyl ester. Total material obtained was 4.1 g (50%) of 9-(2-Benzyloxy-ethyl)-8-chloro-5-methoxy-2,3,4,9,-tetrahydro-1H-carbazole-4-carboxylic acid ethyl ester. The structure was confirmed by $^{13}$C NMR (75 MHz, CDCl$_3$): $\delta_C$ 14.4, 20.5, 22.3, 27.5, 40.2, 43.9, 55.0, 60.2, 70.7, 73.3, 100.2, 107.5, 108.4, 120.1, 122.8, 127.4, 127.5, 128.2, 132.0, 137.4, 138.1, 152.6, and 175.8.

Example 1(g): 9-(2-Benzyloxy-ethyl)-8-chloro-5-methoxy-2,3,4,9,-tetrahydro-1H-carbazole-4-carboxylic Acid To 9-(2-Benzyloxy-ethyl)-8-chloro-5-methoxy-2,3,4,9,-tetrahydro-1H-carbazole-4-carboxylic acid ethyl ester (2.0 g, 4.1 mmol) in ethanol (50 mL) was added sodium hydroxide (1.1 g, 27.1 mmol) and water (5 mL) and heated at 80° C. for 18 h. The ethanol was then removed by evaporation in vacuo and the residue partitioned between diethyl ether (50 mL) and water (50 mL). The diethyl ether layer was separated, dried over magnesium sulfate and concentrated in vacuo to give a gum (71.0 mg). The aqueous layer was acidified to pH 1 with 2N HCl (20 mL) and extracted with dichloromethane (2×100 mL). The dichloromethane layer was dried over magnesium sulfate and concentrated in vacuo to afford 1.6 g (87%) of 9-(2-Benzyloxy-ethyl)-8-chloro-5-methoxy-2,3,4,9,-tetrahydro-1H-carbazole-4-carboxylic acid as a foam. The structure was confirmed by $^{13}$C NMR (75 MHz; CDCl$_3$): $\delta_C$ 20.2, 22.2, 27.1, 39.7, 44.0, 55.1, 70.7, 73.3, 100.6, 106.3, 108.9, 123.0, 127.4, 127.5, 128.3, 132.0, 138.0, and 152.0.

Example 1(h): 9-(2-Benzyloxy-ethyl)-8-chloro-5-methoxy-2,3,4,9,-tetrahydro-1H-carbazole-4-carbonyl Chloride 9-(2-Benzyloxy-ethyl)-8-chloro-5-methoxy-2,3,4,9,-tetrahydro-1H-carbazole-4-carboxylic acid (7) (1.5 g, 3.7 mmol) was dissolved in dichloromethane (50 mL) and oxalyl chloride (700 mg, 5.5 mmol, 470 µL) and DMF (1 drop) were added and the reaction stirred at 20° C. for 2 h. There was a moderate evolution of gas for about 30 min as the reaction proceeded. The reaction was then concentrated in vacuo to give 9-(2-Benzyloxy-ethyl)-8-chloro-5-methoxy-2,3,4,9,-tetrahydro-1H-carbazole-4-carbonyl chloride as a gum which was used into the next step without purification. The structure was confirmed by $^{13}$C NMR (75 MHz; CDCl$_3$): $\delta_C$ 20.8, 22.1, 26.4, 44.2, 51.8, 55.1, 70.7, 73.3, 100.7, 106.0, 108.6, 119.5, 123.4, 127.3, 127.7, 128.3, 131.9, 138.0, 138.2, 152.0. and 176.3.

Example 1(i): 9-(2-Benxyloxy-ethyl)-8-chloro-5-methoxy-2,3,4,9-tetrahydro-1H-carbazole-4-carboxylic Acid Diethylamide 9-(2-Benzyloxy-ethyl)-8-chloro-5-methoxy-2,3,4,9,-tetrahydro-1H-carbazole-4-carbonyl chloride (1.6 g, 3.7 mmol) was then dissolved in dichloromethane (50 mL), cooled to 0° C., stirred and diethylamine (810 mg, 11.0 mmol, 1.1 mL) was added dropwise. The reaction was allowed to warm to room temperature over a period of 18 h. The reaction mixture was then washed with 10% aqueous potassium carbonate (50 mL), separated, dried over magnesium sulfate and concentrated in vacuo to a gum. The crude material was crystallized from diethyl ether to afford 1.2 g (71%) of 9-(2-Benxyloxy-ethyl)-8-chloro-5-methoxy-2,3,4,9-tetrahydro-1H-carbazole-4-carboxylic acid diethylamide as a white crystalline solid. The structure was confirmed by $^{13}$C NMR (75 MHz; CDCl$_3$): $\delta_C$ 13.0, 14.5, 19.8, 22.2, 27.9, 36.4, 40.4, 41.9, 43.8, 55.0, 70.8, 73.3, 100.2, 108.5, 108.6, 119.9, 122.5, 127.4, 127.5, 128.3, 131.5, 137.8, 138.2, 152.4, and 174.5.

Example 1(j): 9-(2-Benzyloxy-ethyl)-5-methoxy-2,3,4,9-tetrahydro-1H-carbazole-4-carboxylic Acid Diethylamine 9-(2-Benxyloxy-ethyl)-8-chloro-5-methoxy-2,3,4,9-tetrahydro-1H-carbazole-4-carboxylic acid diethylamide (1.0 g, 2.1 mmol) in methanol (100 ml) was shaken with 10% palladium on charcoal (1.0 g), triethylamine (2.9 mg, 2.9 mmol, 4 μl) under an atmosphere of hydrogen gas for 18 h at 55° C. The reaction was then filtered through a pad of celite and the filtrate concentrated in vacuo to give a gum (908 mg). The gum was then taken up in dichloromethane (100 ml) and washed with 5% aqueous potassium carbonate solution (50 ml). The dichloromethane solution was then separated, dried over magnesium sulfate and concentrated in vacuo to afford a gum. The gum was then crystallised from diethyl ether (50 ml) and the crystals collected by filtration to afford 523 mg (57%) of 9-(2-Benzyloxy-ethyl)-5-methoxy-2,3,4,9-tetrahydro-1H-carbazole-4-carboxylic acid diethylamine. The structure was confirmed by $^{13}$C NMR (75 MHz; CDCl$_3$): δ$_C$ 13.1, 14.6, 20.1, 22.0, 28.1, 36.4, 40.5, 42.0, 43.0, 54.7, 68.8, 73.3, 99.4, 102.4, 107.8, 116.4, 121.2, 127.6, 127.6, 128.3, 135.6, 137.8, 138.0 153.6, and 175.0.

Example 1(k): 9-(2-hydroxyethyl)-5-methoxy-2,3,4,9-tetrahydro-1H-carbazole-4-carboxylic Acid Diethylamine 9-(2-Benzyloxy-ethyl)-5-methoxy-2,3,4,9-tetrahydro-1H-carbazole-4-carboxylic acid diethylamine (1.0 g, 2.1 mmol) in methanol (50 ml) was shaken with 10% palladium on charcoal (300 mg), and hydrogen gas excess for 18 h at 55° C. The reaction was then filtered through a pad of celite and the filtrate concentrated in vacuo to give 578 mg (100%) 9-(2-hydroxyethyl)-5-methoxy-2,3,4,9-tetrahydro-1H-carbazole-4-carboxylic acid diethylamine as a foam. The structure was confirmed by $^{13}$C NMR (75 MHz; CDCl$_3$): δ$_C$ 13.0, 14.4, 20.0, 22.0, 28.0, 36.4, 40.6, 42.0, 54.7, 60.6, 99.2, 102.6, 107.0, 116.7, 121.1, 136.1, 137.5, 138.0 153.5, and 175.7.

Example 1(l): Methanesulphonic acid 2-(4-diethylcarbamyl-5-methoxy-1,2,3,4-tetrahydro-carbazol-9-yl) Ethyl Ester (Racemic Mixture of the S-Enantiomer and the R-Enantiomer of Compound 1 of Formula I)

9-(2-Hydroxyethyl)-5-methoxy-2,3,4,9-tetrahydro-1H-carbazole-4-carboxylic acid diethylamine (478 mg, 1.4 mmol) in dichloromethane (30 ml) was cooled to 0° C. and methanesulfonyl chloride (477 mg, 4.2 mmol, 324 μL) and triethylamine (420 mg, 4.2 mmol, 578 μL) were added and allowed to warm to RT overnight. The reaction was washed with 5% aqueous potassium carbonate solution. The layers were separated. The combined organics were dried over magnesium sulfate and concentrated in vacuo to give a gum (696 mg). The crude material was purified by silica gel chromatography eluting with petrol (A): ethyl acetate (B) (75-100% B, 22 CV, 120 g, 85 mL/min) to afford Methanesulphonic acid 2-(4-diethylcarbamyl-5-methoxy-1,2,3,4-tetrahydro-carbazol-9-yl) ethyl ester as a gum that crystallised from diethyl ether to give 346 mg (59%) of a colourless solid. The structure was confirmed by $^{13}$C NMR (75 MHz; CDCl$_3$): δ$_C$ 13.1, 14.5, 20.0, 21.9, 28.0, 36.3, 36.7, 40.3, 41.8, 41.9, 54.7, 68.1, 100.0, 102.0, 109.0, 116.4, 122.0 135.1, 137.3, 153.8, and 174.6.

Example 2: Separation of Precursor Compound 1 from its Alternative Enantiomer

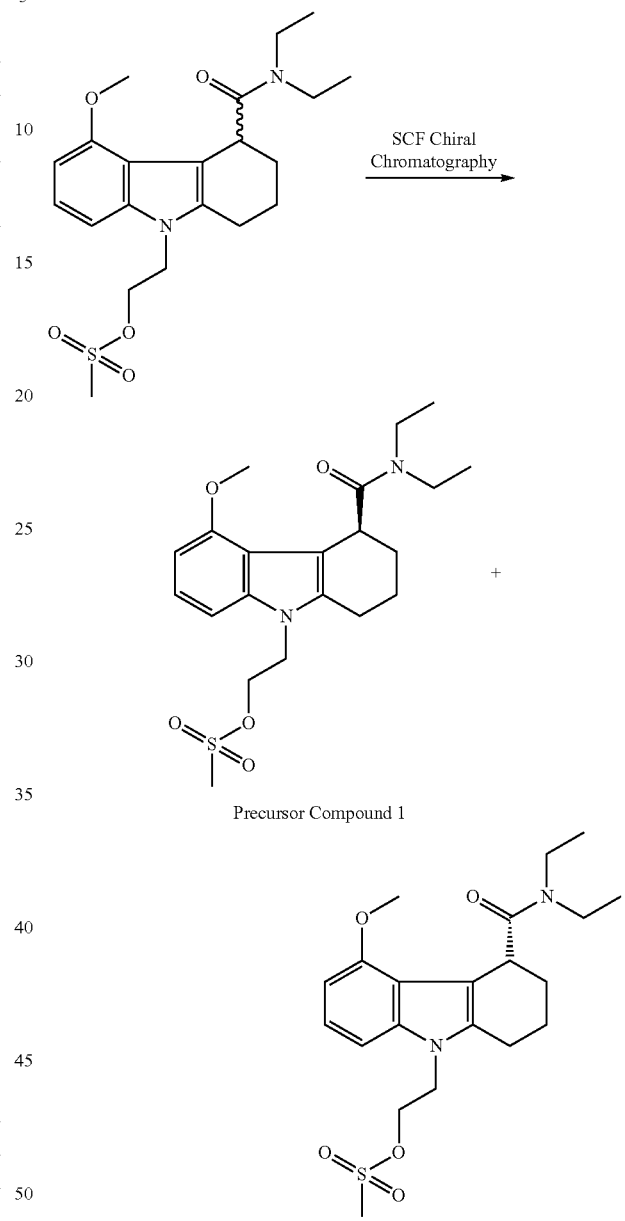

The racemic mixture of Precursor Compound 1 and its alternative enantiomer (obtained as described in Example 1) was separated into its enantiomers using chiral supercritical fluid (CO$_2$) chromatography on a Kromasil Amycoat, 250× 10 mm, 5 μm, 100 Å column using 30% IPA at 40° C. at 13 ml a min with a run time of 6 min. 60 mg of the racemate was dissolved in 1.4-Dioxane (2 ml) and up to 200 μl at a time was as injected for each run. Baseline separation between the two enantiomers was achieved. Analytical HPLC determination of the enantiomeric purity of the two separated enantiomers on an IC from Chiral Technologies, 250×4.6 mm, 5 μm, run isocratic, 80:20-MeOH: IPA at 0.5 ml/min and room temperature indicated an enantiomeric purity of 99.5% of each of the enantiomers.

Comparative Example 3: Purification of Precursor Compound 1 by Rotary Evaporation Precursor Compound 1 and its alternative enantiomer, separated according to the method described in Example 2, were isolated using a rotary evaporator (Heidolph) under reduced pressure (<10 mBar) with a water bath temperature of 39° C.±1° C.

<5 g batches were subjected to rotary evaporation using a bench top rotary evaporator and small size rotary evaporator flasks (1-2 L). No solids were formed, only oils.

In an effort to obtain solid product, the flasks containing the oils were placed in a vacuum oven (Yamato) at 30° C. overnight to try and remove any residual solvent that may have been present. Both enantiomers were then removed from the oven and redissolved in isopropanol (40 ml) and filtered into a clean flask using a 0.2 micron filter with syringe. The flask was then placed back onto the rotary evaporator to dry at 39° C. Upon drying both enantiomers again formed oils.

The evaporation was attempted by dissolving the enantiomers in different solvents (MeCN and alcohols) or in a mixture of solvents. In addition rotary evaporator flask size and rotary evaporation parameters were screened (vacuum, rotation speed and water bath temperature). None of these strategies yielded solid product.

Example 4: Purification of Precursor Compound 1 by Precipitation According to an Embodiment of the Invention 1.6 g of Precursor Compound 1 (the first eluting enantiomer during SFC as described in Example 2) was dissolved into 17 ml of 2-Propanol at 35° C. The resulting solution was diluted slowly with USP water (34 ml) resulting in a precipitate. The mixture was stirred at room temperature for approximately 1 hour followed by stirring at 0-10° C. for approximately 30 minutes. The precipitated solids collected by filtration and allowed to suction dry on a funnel and vacuum dried at 60±5° C. affording 1.45 g (91% recovery).

The same method was carried out with ethanol/water, methanol/water and MeCN/water with similar results.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method comprising:
   separating an S-enantiomer from an R-enantiomer, wherein said S-enantiomer and said R-enantiomer are provided in a racemic mixture and wherein each of said S-enantiomer and said R-enantiomer is a compound of Formula I:

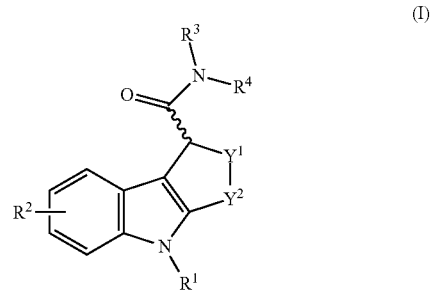

wherein:
$R^1$ is $C_{1-4}$ alkylene-LG wherein LG is a leaving group;
$R^2$ is hydrogen, hydroxyl, halo, cyano, $C_{1-3}$ alkyl, $C_{1-3}$ alkoxy, $C_{1-3}$ fluoroalkyl, or $C_{1-3}$ fluoroalkoxy;
$R^3$ and $R^4$ are independently $C_{1-3}$ alkyl, $C_{7-10}$ aralkyl, or $R^3$ and $R^4$, together with the nitrogen to which they are attached, form a nitrogen-containing $C_{4-6}$ aliphatic ring optionally comprising 1 further heteroatom selected from nitrogen, oxygen and sulfur;
$Y^1$ is O, S, SO, $SO_2$ or $CH_2$;
$Y^2$ is $CH_2$, $CH_2$—$CH_2$, $CH(CH_3)$—$CH_2$, $CH_2$—$CH_2$—$CH_2$ or $CH$—$(CH$—$CH_2$—$CH$—$CH_2)$—$CH$;
said variable bond is above the plane for the S-enantiomer and below the plane for the R-enantiomer as illustrated respectively in Formulas I-S and I-R:

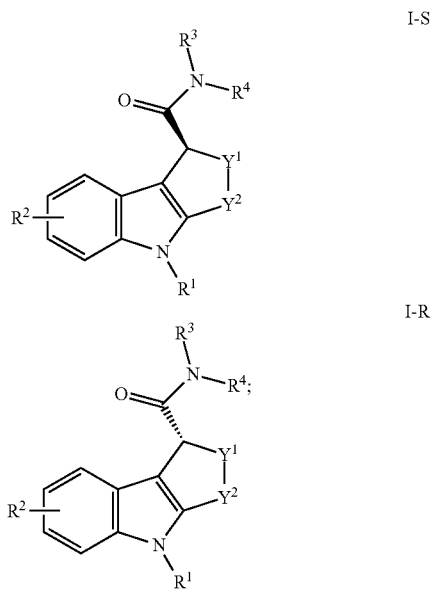

dissolving either one of said separated enantiomers in a suitable organic solvent to obtain a solution;
precipitating said dissolved enantiomer out of the solution wherein said precipitating step comprises addition of water; and
isolating the precipitate.

2. The method as defined in claim 1, wherein $R^1$ is bromo, chloro, iodo, tosylate, mesylate, nosylate or triflate.

3. The method as defined in claim 1, wherein $R^2$ is hydrogen, halo, $C_{1-3}$ alkoxy or $C_{1-3}$ fluoroalkoxy.

4. The method as defined in claim 1, wherein $R^3$ and $R^4$ are independently methyl, ethyl or benzyl.

5. The method as defined in claim 1, wherein $Y^1$ is S.

6. The method as defined in claim 5, wherein $Y^2$ is CH—(CH—CH$_2$—CH—CH$_2$)—CH.

7. The method as defined in claim 1, wherein $Y^1$ is $CH_2$.

8. The method as defined in claim 7, wherein $Y^2$ is $CH_2$—$CH_2$.

9. The method as defined in claim 1, wherein said separating is carried out by supercritical fluid chromatography (SFC).

10. The method as defined in claim 1, wherein said organic solvent is an alcohol, 1,4-dioxane, tetrahydrofuran or acetonitrile.

11. The method as defined in claim 10, wherein said organic solvent is selected from 2-propanol, ethanol, methanol and acetonitrile.

12. A method to obtain an $^{18}$F-labelled PET tracer of Formula II:

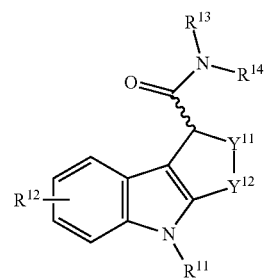

(II)

wherein $R^{11}$ is $C_{1-3}$ alkylene-$^{18}$F;

wherein each of $R^{12}$-$R^{14}$ and $Y^{11}$-$Y^{12}$ is respectively as defined for $R^2$-$R^4$ and $Y^1$-$Y^2$ in claim 1; and wherein said method comprises reacting a solution of said isolated precipitate obtained in claim 1 with a suitable source of $^{18}$F-fluoride to obtain the trace of Formula II.

13. The method as defined in claim 12 which is automated.

* * * * *